(12) United States Patent
Lin et al.

(10) Patent No.: US 10,300,464 B2
(45) Date of Patent: May 28, 2019

(54) CATALYTIC CONVERSION OF BIO-MASS DERIVABLE ALIPHATIC ALCOHOLS TO VALUABLE ALKENES OR OXYGENATES

(71) Applicant: EverNu Technology LLC, Warminster, PA (US)

(72) Inventors: Manhua Lin, Maple Glen, PA (US); Wai-si Eng, Maple Glen, PA (US)

(73) Assignee: EverNu Technology, LLC, Warwick, PA (US)

(*) Notice: Subject to any disclaimer, the term of this patent is extended or adjusted under 35 U.S.C. 154(b) by 0 days.

(21) Appl. No.: 14/649,929

(22) PCT Filed: Dec. 6, 2013

(86) PCT No.: PCT/US2013/073536
§ 371 (c)(1),
(2) Date: Jun. 5, 2015

(87) PCT Pub. No.: WO2014/089412
PCT Pub. Date: Jun. 12, 2014

(65) Prior Publication Data
US 2015/0266005 A1    Sep. 24, 2015

Related U.S. Application Data

(60) Provisional application No. 61/734,411, filed on Dec. 7, 2012.

(51) Int. Cl.

| | | |
|---|---|---|
| C07C 67/36 | (2006.01) |
| B01J 23/888 | (2006.01) |
| C07C 45/38 | (2006.01) |
| C07C 51/235 | (2006.01) |
| C07C 1/24 | (2006.01) |
| B01J 23/28 | (2006.01) |
| B01J 35/02 | (2006.01) |
| B01J 37/00 | (2006.01) |
| B01J 23/00 | (2006.01) |
| B01J 23/30 | (2006.01) |
| B01J 23/68 | (2006.01) |
| B01J 37/08 | (2006.01) |
| C07C 67/40 | (2006.01) |

(52) U.S. Cl.
CPC ......... *B01J 23/8885* (2013.01); *B01J 23/002* (2013.01); *B01J 23/28* (2013.01); *B01J 23/30* (2013.01); *B01J 23/687* (2013.01); *B01J 23/888* (2013.01); *B01J 35/023* (2013.01); *B01J 37/0036* (2013.01); *B01J 37/08* (2013.01); *C07C 1/24* (2013.01); *C07C 45/38* (2013.01); *C07C 51/235* (2013.01); *C07C 67/40* (2013.01); *B01J 2523/00* (2013.01); *C07C 2523/10* (2013.01); *C07C 2523/18* (2013.01); *C07C 2523/22* (2013.01); *C07C 2523/28* (2013.01); *C07C 2523/30* (2013.01); *C07C 2523/745* (2013.01); *C07C 2523/888* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,035,418 A | 7/1977 | Okada |
| 4,249,019 A | 2/1981 | Tamura |
| 4,954,650 A | 9/1990 | Abe |
| 5,144,090 A | 9/1992 | Honda |
| 5,380,933 A | 1/1995 | Ushikubo |
| 6,180,825 B1 | 1/2001 | Lin |
| 6,383,978 B1 | 5/2002 | Bogan |
| 6,403,525 B1 | 6/2002 | Chaturvedi |
| 6,407,280 B1 | 6/2002 | Chaturvedi |
| 6,514,901 B1 | 2/2003 | Lin |
| 6,514,903 B2 | 2/2003 | Lin |
| 6,518,216 B1 | 2/2003 | Han |
| 6,589,907 B2 | 7/2003 | Chaturvedi |
| 6,653,253 B1 | 11/2003 | Lin |
| 6,812,366 B2 | 11/2004 | Lin |
| 6,933,407 B2 | 8/2005 | Berndt |
| 7,049,466 B2 | 5/2006 | Bogan |
| 7,888,281 B2 | 2/2011 | Lin |
| 2008/0177106 A1 | 7/2008 | Lin |

(Continued)

FOREIGN PATENT DOCUMENTS

| | | |
|---|---|---|
| CN | 101652181 A1 | 2/2010 |
| EP | 0168826 B1 | 5/1988 |
| WO | WO 2012/010923 A1 * | 1/2012 |

OTHER PUBLICATIONS

Eguchi et al. The Chem. Society of Japan, Nippon Kagaku Kaishi 1989, 4, p. 660-665.*
Machine translation for Eguchi et al. The Chem. Society of Japan, Nippon Kagaku Kaishi 1989.*
M. Lin, "Selective oxidation of propane to acrylic acid with molecular oxygen" Applied Catalysis A: General, 207 (2001) 1.
D. Tyler et al, "New Catalyst for MMA Process", Chemistry Views, Aug. 22, 2012 (Abstract).
K. Nagai, "New developments in the production of methyl methacrylate" Applied Catalysis A: General 221 (2001) 367.
F. Cavani et al. "Main aspects of the selective oxidation of isobutane to methacrylic acid catalyzed by Keggin-type polyoxometalates" Catalysis Today, 71 (2001) 97-110.

(Continued)

*Primary Examiner* — Ana Z Muresan
(74) *Attorney, Agent, or Firm* — Waisi Eng

(57) ABSTRACT

Disclosed is a method for producing, among others, alkenes and/or saturated or unsaturated oxygenates and, which include at least one of an aldehyde and an acid, comprising subjecting the corresponding C3 to C5 aliphatic alcohols that are derivable from biomass, to a vapor phase process over the catalytic system in the presence of a gas mixture of oxygen, air or nitrogen and/or other suitable diluting gas. The catalyst system comprises multi-catalytic zones, in each of which the composition of the co-feed and other reaction parameter can be independently controlled.

4 Claims, No Drawings

(56) References Cited

U.S. PATENT DOCUMENTS

2008/0261230 A1 10/2008 Liao
2010/0221800 A1 9/2010 Liao
2011/0190464 A1 8/2011 Dubois
2011/0262982 A1 10/2011 Liao

OTHER PUBLICATIONS

L. Wackett, "Microbial-based motor fuels: science and technology" Microbial Biotech, 1 (2008) 211-225.
L. Young, "PCT Notification of Transmittal of International Search Report and Written Opinion", Mar. 27, 2014.
A. Wittmann-Regis, "PCT International Preliminary Report on Patentability", Jun. 9, 2015.
1st Office Action of the Chinese Intellectual Property Office, dated Oct. 23, 2014.
2nd Office Action of the Chinese Intellectual Property Office, dated Dec. 20, 2016.
3rd Office Action of the Chinese Intellectual Property Office, dated Sep. 12, 2017.

* cited by examiner

CATALYTIC CONVERSION OF BIO-MASS DERIVABLE ALIPHATIC ALCOHOLS TO VALUABLE ALKENES OR OXYGENATES

CROSS-REFERENCE TO RELATED APPLICATIONS

This application is the U.S. National Stage of International Application No. PCT/US2013/073536, filed on Dec. 6, 2013, which claims benefit of U.S. Provisional Patent Application No. 61/734,411, filed on Dec. 7, 2012. The entire disclosure of each of the aforesaid applications is incorporated by reference in the present application.

STATEMENT REGARDING FEDERAL SPONSORED RESEARCH OR DEVELOPMENT

The present invention was made with funds provided by the United State Department of Energy under Grant No. DE-SC0007695. The U.S. Government has certain rights in this invention.

FIELD OF THE INVENTION

The present invention relates to a catalytic system and related processes for preparing oxygenates and other valuable products by subjecting an aliphatic alcohol, having a carbon number from 3 to 5 with a straight or branched chain, that is derivable from renewable sources, such as bio-mass, or from $CO_2$, to vapor phase process over a catalytic system of at least one catalyst zone in the presence of air or oxygen as the oxidant. The resulting product can be the corresponding C3 to C5 alkene, aldehydes, unsaturated carboxylic acids, or a mixture thereof. The present invention further relates to a process for preparing a solid catalyst used in the catalytic system useful for the above-mentioned processes for preparing the product oxygenates, and to the catalyst(s), per se.

In particular, the present invention relates to a catalytic process, using air or oxygen as the oxidant, which effectively and efficiently converts a C3 aliphatic alcohol that is derivable from renewable resources (such as bio-mass), either 1- or 2-propanol, or, 1,2- or 1,3-propanediol and/or a mixture thereof, to the corresponding alkene and aldehydes and/or carboxylic acid, i.e., propylene, propyl aldehyde, acrolein and/or acrylic acid, or a C4 aliphatic alcohol that is derivable from such renewable resources, e.g., 2-methyl-propan-1-ol, to the corresponding alkene, aldehydes and/or carboxylic acid, i.e., isobutylene, isobutyl aldehyde, methacrolein and/or methacrylic acid, and to preparation of the catalyst(s) involved, per se.

DESCRIPTION OF THE RELATED ART

It has been well documented that aliphatic alcohols having carbon number from 3 to 5 with a straight chain or branched structure can be biochemically and/or chemically derived from renewable sources, such as bio-mass, and they have high potential to serve as feedstock for certain chemical processes to be developed for manufacturing various valuable chemicals or monomers that are useful building blocks for a broad range of polymer products. Currently, these chemicals or monomers are produced from fossil fuel-derived feedstock, the overexploitation of which by humans has unfortunately led to not only a substantial depletion of such non-renewable resources, but also an alarmingly rapid accumulation of greenhouse gases, thus significantly increasing the level of threats to our long-term energy and national security, ecological and environmental balances, and climate conditions. More importantly, the over dependence on fossil fuels as the predominant source of energy and chemical feedstock can expose countries and businesses alike to critical economic and social uncertainties as a substantial percentage of crude oil produced is used to make chemicals and produce related industrial and consumer goods, a key element of many countries' economies.

While the use of various other types of renewable resources, such as solar, wind and geothermal have been tapped to support other sustainable energy needs, the need for sustainable production of carbon-based fuels and chemicals can only be met by the utilization of renewable biomass. Many countries and regions in the world are rich in sustainable biomass resources. Novel technologies are being developed aiming at affordable and sustainable utilization of various biomass resources, including the utilization of food-grade and/or nonfood biomass, as well as industrial waste, e.g., $CO_2$.

Carbohydrates, such as aliphatic alcohols, are among the most abundant products derivable from sustainable biomass, including cellulose fractions of biomass feedstock. Carbohydrates contain significant amounts (up to more than half) of oxygen by weight and thus can serve as good starting materials to make a range of oxygenated chemical building blocks, such as polymeric monomers to be polymerized alone (homopolymers) or with other monomers (copolymers) to produce commercially important polymer products. These important chemicals or monomers include certain aldehydes and unsaturated carboxylic acids, such as propylene, acrolein, acrylic acid, isobutylene, methacrolein and methacrylic acid, which can also serve as starting materials for the production of the corresponding esters, such as alkyl acrylate and alkyl methacrylate. Acrylic and methacrylic esters are useful as building blocks for numerous polymer products, such as plastic sheets and parts, paints and other coatings, adhesives, caulks, sealants, plastic additives, detergents, and the like.

Acrylic acid (AA) is a very important commodity monomer with annual demands of about 2.9 billion and 11 billion pounds in the US and worldwide, respectively (ICIS Chemical Profiles). Its commercial production is based on a two-step catalytic process developed in the 1970s, wherein propylene is converted to acrolein in the first step, which is further oxidized to AA in the second step. Alternatively, AA can be produced via a one-step oxidation of propylene at a lower overall yield of about 70%. Propylene, the common feedstock for the two aforementioned manufacturing processes, is currently not derived from sustainably renewable sources but from fossil fuel-based sources.

Over the years, various alternative processes have been explored to replace propylene with a cheaper feedstock propane for AA production (M. Lin, *Applied Catalysis A: General*, 207 (2001) 1). The most notable is the development of a class of unique and effective MoVTeNb-based metal oxide catalytic systems for the one-step oxidation of propane, as disclosed in U.S. Pat. Nos. 5,380,933, 6,180,825, 6,514,901, 6,514,903 and 7,049,466. The use of the same MoVTeNbO-based catalysts for the production of acrylic acid from propylene, acrolein and isopropanol are disclosed in U.S. Pat. Nos. 6,653,253 and 6,812,366. For this same class of MoVTeNb oxides, a set of five distinctive XRD peaks at 22.1, 28.2, 36.2, 45.2, and 50 two-theta were first disclosed in U.S. Pat. No. 5,380,933 and later confirmed in U.S. Pat. Nos. 6,180,825 and 6,653,253, as well as in dozens of subsequent patents and journal publications. Such a distinctive set of five XRD peaks were still present in the class of so-called "promoted" MoVTeNbY oxide catalysts, where Y is a promoter incorporated in very small quantity into the basic crystal structure of the MoVTeNb oxides. Examples of the class of promoted catalysts, with Y being Se, Bi, In, Re, Zn, Ga, Pd, Ni, Au or other elements, are disclosed in U.S. Pat. Nos. 6,383,978, 6,403,525, 6,407,280, 6,518,216, 6,589,907 and many other publications. Insofar as is known, none of the above-mentioned propane oxidation processes has been commercialized to date. Furthermore, the lower cost feedstock, propane, is still a fossil fuel-based feedstock.

Another important commodity monomer is methacrylic acid (MAA), of which the ester derivative methyl methacrylate (MMA) has annual demand of about 2.1 billion and 8.1 billion pounds in the US and worldwide, respectively (ICIS Chemical Profiles). The predominant commercial process utilized for producing MAA (or MMA) is known as the ACH process. Even though it was first developed and commercialized in the 1930s, the ACH process is still widely used worldwide for industrial productions of MAA and/or, MMA. The first step of the ACH process uses acetone and hydrogen cyanide as the starting materials. The resulting intermediate cyanohydrin is subsequently converted to a sulfate ester in the second step with an excess amount of concentrated sulfuric acid as the catalyst and solvent. The third step is a hydrolysis step leading to MAA, or an esterification step with methanol leading to MMA. The main drawbacks of this ACH process are its utilization of toxic HCN, the need for the usage and recycling of a large quantity of corrosive sulfuric acid, and the generation of large quantities of ammonium bisulfate and other toxic wastes. For each kilogram of MMA produced, about 2 Kg of sulfuric acid is used and about 2.5 kg of corrosive and useless sulfates are generated for disposal (D. Tyler et al, New Catalyst for MMA Process, *Chemistry Views*, Aug. 22, 2012).

To overcome the drawbacks of the ACH process, various alternative processes have been explored over the years for the production of MAA or MMA. The first alternative process is the two-step direct oxidation process for MAA production from isobutylene. This direct oxidation process was developed and subsequently commercialized by Mitsubishi Rayon, Sumitomo and Kyodo Monomer, respectively, in 1982 in Japan (K. Nagai, *Applied Catalysis A: General* 221 (2001) 367). In this process, isobutylene is converted to methacrolein in a first reactor using a MoBiFeCo containing catalyst (derived from the well-known SOHIO Mo—Bi oxide) as its basic elements, while the resulting methacrolein is further oxidized in a second reactor over heteropoly compounds which contain MoP as the key elements and exhibit Keggin-type structures. An overall MAA yield up to 69% was reported (U.S. Pat. No. 4,954,650 to Abe et al). Another alternative process was developed and commercialized by Asahi in 1998, which produces MMA from isobutene in two steps. In the first step, isobutylene is converted to methacrolein using the same MoBiFeCo oxide catalyst used in the direct oxidation process. In the second step, methacrolein is directly converted to MMA in the liquid phase using a Pd—Pb containing catalyst, which achieves up to 93% yield of MMA from methacrolein (U.S. Pat. No. 4,249,019 to Tamura et al).

Other than the two above-mentioned isobutylene processes, two C2 processes utilizing ethylene, CO and formaldehyde as the corresponding feedstock were also developed and commercialized in 1989 and 2008 by BASF and Lucite, respectively. Today, even decades after the successful commercialization of these alternative isobutylene and ethylene processes, the ACH process is still the dominant industrial process worldwide for producing MAA or MMA.

In addition to isobutene as feedstock used in the two above-mentioned alternative processes, isobutane, which is relatively cheaper and more abundant, has been explored extensively as another potential C4 feedstock for the production of MAA via gas phase catalytic oxidation. Compared with the ACH process or other processes involving isobutylene or t-butanol as feedstock, the isobutane process is considered to have the most potential economic benefits, because the cost of isobutane is significantly lower than all other feedstock, e.g., isobutylene, t-butanol or acetone and HCN for the ACH process. In the 1990s, various substituted Keggin-type heteropoly compounds were reported to exhibit modest activities in converting isobutane to MAA in gas phase oxidation (F. Cavani et al. *Catalysis Today*, 71 (2001) 97-110). However, these Keggin-type heteropoly compounds tend to suffer from short catalytic lifetime at high temperatures required for isobutane oxidation. No reported research in this area over the last two decades has led to any substantial improvements over the catalytic activity or lifetime. As such, Keggin-type heteropoly compounds, as a class of catalysts, remain unsuitable for industrial applications.

Instead of subjecting isobutane to a direct oxidation process, U.S. Pat. No. 6,933,407 to Berndt et al. discloses a process for the production of MAA from isobutane via a three-step process using three different catalysts in three different reactors. The first reactor is a dehydrogenation reactor using Pt-containing metal catalysts as disclosed in various earlier patents. In the dehydrogenation reactor, isobutane is converted to isobutylene and gaseous $H_2$, which is removed before the product mixture of isobutylene and unreacted isobutane is fed to the second reactor. In the second reactor, isobutylene is converted to methacrolein, which is then separated from the unreacted isobutane and fed to the third reactor, where it is converted to MAA. The catalysts used in the second and third reactors are metal oxides and heteropoly compounds respectively, the same as those previously disclosed by other patents including U.S. Pat. No. 4,954,650 mentioned above. Overall, the one-pass conversion of isobutane was reported to be around 25% and one-pass MAA yield was around 9%.

U.S. Pat. No. 7,888,281 to Lin et al. discloses a class of metal oxide catalysts containing three or more metal elements including, for example, Mo, W, Zr, Bi and Te as the basic components for a one-step gas phase process for the production of MAA from isobutane, which achieved a one-pass isobutane conversion of about 20-30%, with the formation of methacrolein and MAA at a combined selectivity of up to about 70%.

Despite the extensive research mentioned above, none of the processes involving isobutane as the feedstock, either in one-step or three-steps, over Keggin-type heteropoly compounds or metal oxide catalysts, are satisfactory for commercial applications.

In addition to the aforementioned two-step isobutene process for MAA production, Mitsubishi Rayon also disclosed in the late 1980s the use of the same class of PMo containing heteropoly compounds as catalysts for isobutanol oxidation to MAA. The isobutanol conversion was complete and the combined methacrolein and MAA yield/selectivity achieved was up to 44% (EP 0168826 B1). However, as illustrated by the comparative examples to this invention, the short catalytic lifetime of this class of PMo containing Keggin-type heteropoly compounds at the required reaction temperature remains a serious defect for industrial application. Since then, no follow-up efforts have been disclosed either by Mitsubishi Rayon or others concerning these heteropoly compounds or other catalysts for isobutanol oxidation, which is likely due to the fact that isobutanol derived from fossil fuel-based sources (such as, from either propylene or isobutylene) is economically uncompetitive as a feedstock for MAA production, and/or due to the detrimental short catalytic lifetime of the PMo containing Keggin-type heteropoly compounds.

Notwithstanding any benefits arising from the aforementioned alternative processes for the production of AA or MAA, all of the corresponding feedstock involved (i.e., propane, isobutane and isobutene) are fossil fuel-based and thus contribute to substantial net $CO_2$ emission. Far more desirable feedstocks for manufacturing these valuable aldehydes and carboxylic acids are those sustainable ones derived from renewable biomass. In this regard, C3 and C4 aliphatic alcohols derived from renewable biomass are suitable feedstocks for the sustainable manufacturing of AA and/or MAA. For instance, direct production of isobutanol from glucose and biomass, such as cellulose, has been accomplished through the use of various biotechnologies, such as the so-called consolidated bioprocessing (CBP) technology, as disclosed in US Patent application 20110262982 by James Liao et al. and also in US Patent application 20080261230 by Der-Ing Liao et al. Such CBP technology is also useful for the production of 1- or 2-propanol from biomass, as disclosed in US Patent applications 20100221800 and 20110262982 by James Liao et al. Currently, the field is rather unexplored for the development of new chemical processes to enable the conversion of such biomass-derived C3 and C4 aliphatic alcohols to those higher-value chemicals, such as AA and MAA, that are currently produced only from fossil fuel-based feedstocks.

SUMMARY OF THE INVENTION

This invention concerns an effective process for utilizing aliphatic alcohols that are derivable from biomass, such as propanol, propanediols or isobutanol, in one-step conversion to produce alkene, aldehyde and/or the corresponding unsaturated carboxylic acid, representative products including propene, acrolein and acrylic acid, or isobutene, isobutyl aldehyde, methacrolein and methacrylic acid.

According to one aspect of the present invention, there is provided a solid metal oxide catalyst comprising a compound having the formula $A_aSb_bX_xY_yZ_zO_n$ wherein A is Mo or W, X is an element selected from the group of Ca, Ce, Co, Fe, Ga, Mg, Ni, Sn, V, W and Zn, Y is one or more element selected from the group of Ag, Au, B, Cr, Cu, La, Li, Mg, Mn, Mo, Na, Nb, Ni, P, Pb, Rb, Re, Ru, Ti, and Z is one or more element from the X or Y groups or from the following: Ba, Cs, K, Pd, Pt and Sr, or mixtures thereof, and wherein a=1, 0.05<b<1.5, 0.01<x<1, 0≤y<0.5, 0≤z<0.2 and n is dependent on the oxidation state of the other elements. Alternatively, there is provided a solid metal oxide catalyst comprising a compound having the formula $A_aX_xY_yZ_zO_n$ wherein A is Mo or W, X is an element selected from the group of Ca, Ce, Co, Fe, Ga, Mg, Ni, Sb, Sn, V, W and Zn, Y is one or more elements selected from the group of Ag, Au, B, Cr, Cu, La, Li, Mn, Mo, Na, Nb, P, Pb, Rb, Re, Ru, Ti, and Z is one or more element from the X or Y groups or from the following: Ba, Cs, K, Pd, Pt and Sr, or mixtures thereof, and wherein a=1, 0.05<x<1.5, 0≤y<1, 0≤z<0.5 and n is dependent on the oxidation state of the other elements.

In another aspect, the present invention provides a process for preparing the above-described solid catalysts, which comprises the following steps:

a) forming a mixture comprising appropriate amounts of source materials containing selected ones of the aforementioned elements to provide such elements in predetermined a, b, x, y and z ratios or a, x, y and z ratios and, optionally, at least one liquid substance in an amount sufficient to provide a solution or slurry of the source materials;

b) removing from said mixture part or all of the liquid substance(s), if present, to obtain a solid catalyst precursor; and c) calcining the catalyst precursor at a temperature from 150° C. to 900° C. under an atmosphere containing oxygen, or an inert gas or a mixture thereof, to yield the solid catalyst.

According to still another aspect, the present invention provides a process of using the above-described catalyst for the production of alkene, aldehyde and/or unsaturated carboxylic acid from an aliphatic alcohol of the same carbon number. This method comprises subjecting a feed gas mixture including an aliphatic alcohol and air, oxygen or nitrogen, and/or one or more inert diluting gases, when needed, to a vapor phase oxidation in a heated reactor, which can have a single or multiple reaction zone(s), with each zone independently comprising a solid compound having the catalyst composition described herein and this catalyst composition may be different from that in another zone, while in each zone the composition of alcohol feed and other co-feed and other reaction parameter can be independently controlled. In the case where propanol or propanediol or the mixture is subjected to a vapor phase catalytic reaction in the presence of a co-fed gas, which is oxygen, air or nitrogen or other diluting gas, the product is at least one of propene, propyl aldehyde, acrolein and acrylic acid. In the case where isobutanol is subjected to such a reaction, the product is at least one of isobutene, isobutyl aldehyde, methacrolein and methacrylic acid.

DETAILED DESCRIPTION OF THE INVENTION

The present invention concerns a catalytic system of complex metal oxides, its method of preparation and its use for producing an alkene and various oxygenates, such as aldehydes and/or carboxylic acids (e.g., propene, isobutene, propyl and isobutyl aldehydes, acrolein and/or acrylic acid, as well as methacrolein and/or methacrylic acid), by subjecting an appropriate aliphatic alcohol that is derivable from biomass, such as one of 1- or 2-propanol, or 1,2- or 1,3-propanediol or a mixture thereof, or isobutanol, to gas phase oxidation in the presence of air or oxygen under certain conditions over the metal oxide catalytic system having the specific composition described herein, which may be a bulk solid substance or a substance dispersed onto and/or into a support material of high surface area. The catalyst system consists of a single or multi-catalytic zone(s), in each of which the composition of the co-feed and other reaction parameter can be independently controlled/adjusted. The present invention can be applied to various C3-C5 aliphatic alcohols that are derived from biomass for the production of the corresponding alkenes and/or other oxygenates having the same number of carbon atoms as the original alcohol. For instance, when 1-propanol or 2-propanol or 1,2-propanediol or 1,3-propanediol or a mixture thereof is subjected to a vapor phase catalytic process over the above-described catalytic system in the presence of a co-fed gas, which is oxygen or air, with or without nitrogen or other diluting gas, the product is at least one of propylene, propyl aldehyde, acrolein and acrylic acid. In the case where isobutanol is subjected to such a process, the product is at least one of isobutene, isobutyl aldehyde, methacrolein and methacrylic acid.

In carrying out the method of the invention, suitable aliphatic alcohols and co-fed gas(es) are caused to undergo gas-phase reaction in the presence of a complex metal oxide catalytic system of a single or multi-catalytic zones, in each of which the alcohol feed and the composition of the co-feed, as well as other reaction parameters can be independently controlled. Each catalytic zone comprises a compound having the basic formulas $A_aSb_bX_xY_yZ_zO_n$ or $A_aX_xY_yZ_zO_n$ wherein A, X, Y, Z, a, b, x, y, z and n, are as previously defined.

In one embodiment, the catalyst of the invention has the above formula $A_aSb_bX_xY_yZ_zO_n$, wherein A is Mo or W, X is an element from the group of elements Ce, Fe, Ga, Mg, Sn, V, W, Zn, and Y, if present, is at least one of the group of elements Ag, Au, B, Cu, La, Mn, Mo, Nb, P, Ti, and Z, if present, is at least one of the elements from the X group, Y group or Ba, Cs, K, Pd and Pt. Alternatively, the catalyst of the invention has the above formula $A_aX_xY_yZ_zO_n$, wherein A is Mo or W, X is an element from the group of Ce, Fe, Ga, Mg, Sb, Sn, V, W and Zn, and Y, if present, is at least one of the group of elements Ag, Au, B, Cu, La, Mn, Mo, Nb, P, Ti and Z, if present, is at least one of the elements from the X group, Y group or Ba, Cs, K, Pd and Pt.

In another embodiment, the catalyst of the invention has the above formula $A_aSb_bX_xY_yZ_zO_n$, wherein A is Mo or W, X is one of elements Ce, Fe, V and W, Y, if present, is at least one of the group of elements Ag, Au, Mo, Nb, P and Ti, and Z, if present, is at least one element from the X group, Y group or Ba, Cs and Pd. Alternatively, the catalyst of the invention has the above formula $A_aX_xY_yZ_zO_n$, wherein A is Mo or W, X is one of elements Ce, Fe, Sb, V and W, Y, if present, is at least one of the group of elements Ag, Au, Mo, Nb, P and Ti, and Z, if present, is at least one element from the X group, Y group or Ba, Cs and Pd.

The solid mixed metal oxide catalysts of this invention are not heteropoly compounds including heteropoly acids or their salts that may or may not exhibit Keggin-type structures. Furthermore, the solid mixed metal oxide catalysts of this invention do not require more than two or three metal elements, although optionally, the catalysts of this invention may contain more than two or three metal elements. Specifically, the solid mixed metal oxide catalysts of this invention do not contain elements Bi, Se or Te, and do not exhibit the set of five distinctive XRD peaks at 22.1, 28.2, 36.2, 45.2, and 50 two-theta that characterize the class of catalysts based on mixed MoVTeNb oxides (including the "promoted" ones) as disclosed by many of the above-mentioned patents. Thus, the chemical composition, and hence the resulting structure and catalytic properties of the catalysts of this invention, is distinctively different from any of the catalysts in the related art discussed above. The catalytic system comprising mixed metal oxide catalysts as described herein with the general formula $A_aSb_bX_xY_yZ_zO_n$ or $A_aX_xY_yZ_zO_n$ are specifically effective in producing, among others, propylene, propyl aldehyde, acrolein and/or acrylic acid from biomass-derived C3 alcohols and isobutylene, isobutyl aldehyde, methacrolein and/or methacrylic acid from biomass-derived isobutanol.

The mixed metal oxide catalysts with the general formula $A_aSb_bX_xY_yZ_zO_n$ or $A_aX_xY_yZ_zO_n$ can be prepared in the following manner.

The first step is the preparation of a catalyst precursor, which is a solid substance containing all of the essential metal elements, and which will lead to a mixed metal oxide catalyst after being subjected to calcination at elevated temperatures. The sources of each element used for the preparation of such a precursor can be selected from a wide range of materials, including oxides, halides, nitrates, alkoxides, oxalates, hydroxides, acetates, or various other organometallic compounds containing the element, or metal elements in the form of fine metal particles. The forms of these materials can be a liquid, a solution, a slurry or a solid. Thus, the mixing of source materials can involve the mixing of one or more individual liquids, solutions, slurries or solids. When all elements are introduced in solid form, the resulting solid mixture can be further ground to enhance the thorough mixing of the elements. When one or more elements are introduced as a solution or a slurry, the liquid substances that are suitable as a source material for the preparation of the solution or slurry can be selected from water or various other organic liquids, such as alcohols, ketones, ethers, acids, and aliphatic or aromatic compounds. The solid catalyst precursor can be obtained after the partial or complete removal of the liquid substance(s) or solvent(s) from the mixture. The liquid substance(s) or solvent(s) can be removed using various methods, including air-drying, freeze-drying, spray drying, filtration, rotary evaporation, or evaporation under reduced pressure and/or various temperatures. Various other techniques known in the art, such as hydrothermal synthesis, sol-gel process, col-gel process, or various precipitation techniques can also be applied for the preparation of the catalyst precursor.

The catalyst precursor thus obtained is then calcined at suitable temperatures in proper stages for a suitable amount of time and under a suitable atmosphere for each stage to form the desired metal oxide catalyst. A suitable atmosphere can be different for each calcination stage, and may be inert, such as nitrogen or argon (the latter being more preferred), or oxidative, such as air, or reducing, such as hydrogen. The calcination temperature usually starts at close to room temperature and then is raised to a different temperature for each of the later stages ranging from about 150° C. to 900° C. The preferable temperature for the higher calcination stage is from 450° C. to 700° C. Likewise, the duration for each calcination stage can be different. Typically, the overall calcination is performed from 1 to 30 hours and preferably, the duration of the high temperature stage is from 2 to 10 hours, to obtain a desirable mixed metal oxide catalyst having the formula $A_aSb_bX_xY_yZ_zO_n$ or $A_aX_xY_yZ_zO_n$ wherein A, X, Y, Z and a, b, x, y, z and n are as defined above. As previously noted, the molar ratio, n, i.e., the amount of oxygen (O) present in the finished catalyst is dependent on the oxidation state and the ratio of the other elements in the catalyst.

The mixed metal oxides, thus obtained as a bulk solid catalyst, exhibits excellent catalytic properties when used as is. However, improved catalytic performance can be attained by grinding the resulting metal oxide to fine particles. The mixed metal oxides thus obtained may also be incorporated, at different preparation stages, onto and/or into a high surface area support material, using various techniques well known in the art. Suitable support materials include, without limitation, oxides, carbides, or nitrides of one or more element from the group of Al, Mg, Nb, Si, Ti, and Zr or composites thereof. The support material can be in the form of various structures selected from particles, fibers, ceramic foam, monolith or fabric. The dispersion of the elements of the metal oxide catalyst onto and/or into the suitable support material can be accomplished by various techniques well known in the art, such as wetting, impregnation, sol-gel, co-gel, precipitating, co-precipitating, ion-exchange, vapor depositing, reverse micro-emulsion depositing or a combination thereof. Further, the resulting supported catalysts may be molded into a suitable shape and size depending on the size and shape of the reactor to be used.

Another aspect of the present invention comprises introducing C3-C5 aliphatic alcohols that are derivable from renewable resources in the gas phase into a reactor containing the above described mixed metal oxide, in the presence of air or oxygen and diluting gas(es), when needed, to produce the desired alkene, aldehyde, unsaturated carboxylic acid or mixture thereof. The processes of producing the desired aliphatic alcohols from renewable resources have been documented (see, for instance, US Patent application 20080261230 by Der-ing Liao et al. and US Patent applications 20100221800 and 20110262982 by James Liao et al.) and are thus beyond the scope of the disclosure herein. The aliphatic alcohols thus obtained from renewable resources do not need to be very pure, and can be a mixture thereof, to serve as the feedstock in reactions of this invention in the presence of the above described mixed metal oxide catalyst and can further tolerate the presence of water in a reasonable quantity in the feedstock. However, such aliphatic alcohols may be subjected to prior purification and enrichment step(s), if needed.

In the case where an aliphatic alcohol is subjected to the vapor phase catalytic reaction described herein, the product is at least one or more of the corresponding alkene, aldehyde, and unsaturated acid of the same carbon number. Suitable amounts of water vapor or steam can be incorporated into the feed-gas mixture, which may function as a diluting gas and enhance the selective formation of the desirable oxygenates. Furthermore, inert gas such as nitrogen, argon or helium or a pseudo-inert gas such as carbon dioxide or the like may also be incorporated into the feed gas mixture as diluting gases, if desired. In the case of the production of propylene, propyl aldehyde, acrolein or acrylic acid or a mixture thereof, the feed-gas to the reaction system is a mixture in the appropriate ratios of A) C3 aliphatic alcohol, i.e., 1-propanol, 2-propanol, or 1,2-propanediol or 1,3-propanediol and/or a mixture thereof, that is of reasonable purity obtained from renewable resource through a process detailed elsewhere and outside the scope of this invention; B) oxygen or air, C) inert diluting gas(es), such as nitrogen or argon or helium or carbon dioxide, D) water vapor or steam. The molar ratio of alcohol/(oxygen or air)/inert dilute gas/steam A:B:C:D of the feed-gas mixture can be (1):(0.1 to 20):(0 to 20):(0 to 70). When C3 aliphatic alcohol, which is either 1-propanol, 2-propanol, or 1,2-propanediol or 1,3-propanediol and/or a mixture thereof, is subjected to a vapor phase catalytic reaction in the presence of air or oxygen, the product is at least one or more of propylene, propyl aldehyde, acrolein and acrylic acid.

Similarly in the case of the production of isobutene, isobutyl aldehyde, methacrolein or methacrylic acid or a mixture thereof, the feed-gas to the reaction system is a mixture in the appropriate ratios of A) isobutanol of reasonable purity obtained from a process detailed elsewhere and outside the scope of this invention; B) oxygen or air, C) inert diluting gas(es), such as nitrogen or argon or helium or carbon dioxide, D) water vapor or steam. The molar ratio of isobutanol/(oxygen or air)/inert dilute gas/steam A:B:C:D of the feed-gas mixture can be (1):(0.1 to 20):(0 to 20):(0 to 70). When isobutanol is subjected to a vapor phase catalytic oxidation in the presence of air or oxygen, the product is at least one or more of isobutene, isobutyl aldehyde, methacrolein and methacrylic acid.

The above-mentioned catalytic reaction of aliphatic alcohols can take place utilizing a fixed bed system or a fluidized bed system comprising a single or multiple catalytic zones, in each of which zone the catalyst composition can be different from that in another zone while the molar ratio of alcohol feed and the co-feeds (i.e., oxygen or air/inert dilute gas/water vapor or steam) and other reaction parameter can be independently controlled and thus can be different from one another. This reaction can be conducted at atmospheric pressure or at an elevated pressure. A suitable reaction temperature is from 200° C. to 600° C., but is preferably from 250° to 550° C. The feed-gas preferably flows at a space velocity (SV) range of 360 to 36,000 $hr^{-1}$, with the corresponding feed-gas and catalyst contact time being in the range of 10 to 0.1 seconds. The reaction mixture flowing through all reaction zones (if multiple present) is not withdrawn, isolated or separated midway, but the product stream at the reactor exit can be further separated and the alkene and/or aldehydes therein can be recycled back to feed and/or for further reaction(s).

When a C3 alcohol is subjected to catalytic oxidation according to the present invention, propylene, propyl aldehyde, acrolein and acrylic acid are the desired products. However, other oxidation and partial oxidation products, such as carbon oxides, acetic acid, acetone may also be produced as by-products. In addition to being useful products, propylene and propyl aldehyde are also intermediates which can be further oxidized to acrolein or acrylic acid. Similarly, when isobutanol is subjected to catalytic oxidation according to the present invention, isobutene, isobutyl aldehyde, methacrolein and methacrylic acid are the desired products. However, as stated above, other oxidation and partial oxidation products, such as carbon oxides, acetic acid, acetone, acrylic acid may also be produced as by-products. In addition to being useful products, isobutene and isobutyl aldehyde are also intermediates which can be further oxidized to methacrolein and/or methacrylic acid, both can be further converted to methyl methacrylate (MMA) through processes well-known in the art. The separation of gaseous C3-C4 alkenes or aldehydes from acids is reasonably straight forward via conventional separation technologies, in view of the substantial difference in the boiling points. Thus, this invention provides a catalytic process to produce propylene, propyl aldehyde, acrolein and acrylic acid from a C3 bio-alcohol and isobutylene, isobutyl aldehyde, methacrolein and/or methacrylic acid, and optionally to MMA, from bioisobutanol, respectively.

EXAMPLES

The present invention will now be described more specifically with Examples and Comparative Examples, wherein conversion (Conv.), selectivity (Sel.) and yield (Y.) have the following definition:

Conversion (%)=(moles of aliphatic alcohol(s) consumed/moles of aliphatic alcohol(s) feed)×100;

Selectivity (%)=(moles of product formed/moles of aliphatic alcohol(s) consumed)×100;

Yield (%)=(moles of product formed/moles of aliphatic alcohol(s) feed)×100.

The examples are provided for illustrative purposes only, and are in no way intended to limit the scope of the invention, as set forth in the appended claims.

The catalyst precursors for Catalyst-1 through -7 with the empirical formulas as shown in Table 1 were prepared using one of the aforementioned methods. After calcination at the temperature and atmosphere as specified in Table 1, the mixed metal oxide catalysts thus obtained were ground to a fine powder and pressed in a mold and then broken and sieved to 12-20 mesh granules for the subsequent catalytic testing as described in the Examples.

TABLE 1

Catalysts of this invention used in the Examples

| Catalyst | Empirical formula | Calcination Temp. (° C.) | Atmosphere | Time (h) |
|---|---|---|---|---|
| Cat. 1 | $Mo_1Sb_1V_{0.3}O_n$ | 600 | Argon | 4 |
| Cat. 2 | $Mo_1Sb_{0.5}O_n$ | 600 | Argon | 2 |
| Cat. 3 | $W_1Sb_{0.5}O_n$ | 600 | air | 4 |
| Cat. 4 | $W_1Sb_1O_n$ | 550 | argon | 4 |
| Cat. 5 | $W_1Sb_{0.5}V_{0.1}Ce_{0.1}Fe_{0.02}O_n$ | 600 | Argon | 2 |
| Cat. 6 | $Mo_1Sb_{0.6}V_{0.04}O_n$ | 550 | Argon | 4 |
| Cat. 7 | $Mo_1Sb_1V_{0.3}Sn_{0.03}Ag_{0.01}O_n$ | 550 | Argon | 4 |

Comparative Catalysts-1 through -5 with empirical formulas as shown in Table 2 were prepared/obtained according to the related references/source identified. These catalysts were ground to a fine powder and pressed in a mold and then broken and sieved to 12-20 mesh granules for the subsequent catalytic testing described in the Comparative Examples.

Example 1

Solid mixed metal oxide with an empirical formula of $Mo_1Sb_1V_{0.3}O_n$ and coded as Catalyst-1 in Table 1 was subjected to the evaluation of catalytic performance for isobutanol oxidation. The solid catalyst sample was first ground to a fine powder and pressed in a mold and then broken and sieved to 12-20 mesh granules. About 0.5-1.5 g of these granules were packed in a quartz tubular reactor of 4 mm ID and placed in a temperature programmable tube furnace. The catalytic testing was conducted at 450° C. At slightly above atmospheric pressure, the feed-gas mixture containing about 4% isobutanol vapor and the balance of co-feed gases passed through the catalyst bed at a space velocity of about 2,700 $hr^{-1}$. Two independent temperature-controlled saturators were used to separately control the amounts of isobutanol and water in the feed-gas mixture, while gas-flow controllers were used to control the flow rates of air or nitrogen co-feeds. The reaction effluent was analyzed directly using gas chromatography ("GC") to determine the isobutanol conversion and the yields and selectivity values of the corresponding products. The resulting isobutanol conversion, and selectivity values and yields of the valuable C4 products are shown in Table 3.

TABLE 3

Catalytic Oxidation of Isobutanol to Isobutene and Valuable C4 Oxygenates

| Ex. | Cat. | empirical formula | Co-feed $N_2$/air/water | Temp. (° C.) | Conv. (%) | *Selectivity/Yield (%) | | | | |
|---|---|---|---|---|---|---|---|---|---|---|
| | | | | | | iBE | MAc | iBal | MAA | C4-O |
| E1 | 1 | $Mo_1Sb_1V_{0.3}O_n$ | 20/10/8 | 450 | 100 | 12 | 54 | — | 4 | 58 |
| E2 | 2 | $Mo_1Sb_{0.5}O_n$ | 10/2/0 | 225 | 99 | 4 | — | 79 | — | 79 |
| E3 | 3 | $W_1Sb_{0.5}O_n$ | 30/2/2 | 450 | 100 | 48 | 30 | — | — | 30 |
| E4 | 4 | $W_1Sb_1O_n$ | 20/10/8 | 450 | 100 | 19 | 39 | — | 1 | 40 |
| E5 | 5 | $W_1Sb_{0.5}V_{0.1}Ce_{0.1}Fe_{0.02}O_n$ | 28/5/0 | 540 | 100 | 10 | 51 | — | — | 51 |
| E6 | 5 | Z1: $W_1Sb_{0.5}V_{0.1}Ce_{0.1}Fe_{0.02}O_n$ | Z1: 20/2/0 | Z1: 450 | 100 | 1 | 49 | — | 4 | 53 |
| | 6 | Z2: $Mo_1Sb_{0.6}V_{0.04}O_n$ | Z2: 0/10/2 | Z2: 400 | | | | | | |
| E7 | 4 | Z1: $W_1Sb_1O_n$ | Z1: 20/2/0 | Z1: 300 | 100 | 5 | 50 | — | 2 | 52 |
| | 7 | Z2: $Mo_1Sb_1V_{0.3}Sn_{0.03}Ag_{0.01}O_n$ | Z2: 0/8/2 | Z2: 440 | | | | | | |
| C1 | CC1 | $P_{1.5}Mo_{12}V_{0.8}Cu_{0.4}B_{0.3}Cs_{0.3}On$ | 23/10/5 h1 | 340 | 100 | 38 | 40 | — | 1 | 41 |
| C2 | CC1 | $P_{1.5}Mo_{12}V_{0.8}Cu_{0.4}B_{0.3}Cs_{0.3}On$ | 23/10/5 h2 | 340 | 100 | 45 | 27 | — | 1 | 28 |
| C3 | CC2 | $\gamma$-$Al_2O_3$ | 20/7/0 | 250 | 97 | 10 | 0 | 9 | 0 | 9 |
| C4 | CC3 | $Mo_1Bi_{0.2}O_n$ | 10/10/0 | 225 | 100 | 41 | 5 | 6 | 0 | 11 |
| C5 | CC4 | $W_1V_{0.15}Te_{0.08}Nb_{0.15}O_n$ | 30/2/2 | 450 | 100 | 56 | 10 | 2 | 0 | 12 |

*C1-C3 deep oxidation products are not reported; iBE = isobutene, MAc = methacrolein, iBal = isobutyl aldehyde, MAA = methacrylic acid, C4-O = total C4 oxygenates; Z1 = zone-1, Z2 = zone-2; "CC1" to "CC4" refer to Comparative Catalysts 1 to 4 described in Table 2

TABLE 2

Comparative Catalysts Used in Comparative Examples

| Comparative catalysts | Empirical formula | Reference/source |
|---|---|---|
| Comp. Cat. 1 | $P_{1.5}Mo_{12}V_{0.8}Cu_{0.4}B_{0.3}Cs_{0.3}O_n$ | EP0168826 Ex. 27 |
| Comp. Cat. 2 | $\gamma$-$Al_2O_3$ | From Saint-Gobain |
| Comp. Cat. 3 | $Mo_1Bi_{0.2}O_n$ | SOHIO Mo—Bi oxide |
| Comp. Cat. 4 | $W_1V_{0.15}Te_{0.08}Nb_{0.15}O_n$ | U.S. Pat. No. 6,693,059 |
| Comp. Cat. 5 | $Mo_1V_{0.3}Te_{0.23}Nb_{0.12}O_n$ | U.S. Pat. No. 5,380,933 |
| | | U.S. Pat. No. 6,180,825 |

Example 2 Through 5

Solid mixed metal oxides coded as Catalyst-2 through -5 with the corresponding empirical formulas as listed in Table 1 were subjected to the evaluation of catalytic performance for the isobutanol oxidation in essentially the same manner as described in Example-1. The resulting isobutanol conversion, and the selectivity values and yields of the valuable C4 products are shown in Table 3.

Example 6

Solid mixed metal oxides coded as Catalyst-5 and Catalyst-6 in Table 1 were packed in zone-1 and zone-2 of the catalytic reactor with the reaction mixture flowing through both zones without being withdrawn midway, while the temperature and co-feed gases in each zone were independently controlled as described in Table 3. The evaluation of the catalytic performance for the isobutanol oxidation was carried out in a similar manner as described in Example-1. The resulting isobutanol conversion, and the selectivity values and yields of the valuable C4 products are shown in Table 3.

Example 7

Solid mixed metal oxides coded as Catalyst-4 and Catalyst-7 in Table 1 were packed in zone-1 and zone-2 of the catalytic reactor with the reaction mixture flowing through both zones without being withdrawn midway, while the temperature and co-feed gases in each zone were independently controlled as described in Table 3. The evaluation of catalytic performance for isobutanol oxidation was carried out in a similar manner as described in Example-6. The resulting isobutanol conversion, and the selectivity values and yields of the valuable C4 products are shown in Table 3.

Comparative Examples 1 and 2

Comparative Catalyst-1 in Table 2 was subjected to the evaluation of the catalytic performance for isobutanol oxidation in essentially the same manner as described in Example-1. The resulting isobutanol conversion, and the selectivity values and yields of the valuable C4 products are shown in Table 3. Comparative Example-1 is the corresponding catalytic testing in the first hour, while Comparative Example-2 is the catalytic testing at about an hour after Comparative Example-1.

Comparative Examples 3 Through 5

In essentially the same manner as described in Example-1, Comparative Catalyst-2 through 4, as described in Table 2, were subjected to the evaluation of the catalytic performance for isobutanol oxidation as Comparative Example 3 through 5. The resulting isobutanol conversion, and the selectivity values and yields of the valuable C4 products are shown in Table 3.

Example 8

Solid mixed metal oxide coded as Catalyst-1 in Table 1 was subjected to the evaluation of catalytic performance in essentially the same manner as described in Example-1, except 1-propanol was used in the place of isobutanol. The resulting 1-propanol conversion, selectivity values and yields of the valuable C3 products are shown in Table 4.

Example 9

Solid mixed metal oxides coded as Catalyst-4 and Catalyst-1 in Table 1 were packed in zone-1 and zone-2 of the catalytic reactor with the reaction mixture flowing through both zones without being withdrawn midway, while the temperature and co-feed gases in each zone were independently controlled as described in Table 4. The evaluation of the catalytic oxidation performance was carried out in a similar manner as described in Example-6, except 1-propanol was used in the place of isobutanol. The resulting 1-propanol conversion, selectivity values and yields of the valuable C3 products are shown in Table 4.

Example 10

Solid mixed metal oxides coded as Catalyst-4 and Catalyst-1 in Table 1 were packed in zone-1 and zone-2 of the catalytic reactor with the reaction mixture flowing through both zones without being withdrawn midway, while the temperature and co-feed gases in each zone were independently controlled as described in Table 4. The evaluation of catalytic oxidation performance for was carried out in a similar manner as described in Example-9, except 2-propanol was used replacing 1-propanol. The resulting 2-propanol conversion, selectivity values and yields of the valuable C3 products are shown in Table 4.

Example 11 and 12

Solid mixed metal oxides coded as Catalyst-4 and Catalyst-1 in Table 1 were subjected to the evaluation of the catalytic performance in a similar manner as described in Example-1, except 1,2-propanediol was used in the place of isobutanol. The resulting 1,2-propanediol conversion, selectivity values and yields of the valuable C3 products are shown in Table 4.

TABLE 4

| Catalytic Oxidation of C3 Aliphatic Alcohols to Propene and C3 Oxygenates | | | | | | | | | | |
|---|---|---|---|---|---|---|---|---|---|---|
| | Catalyst | | | Co-feed | Temp. | Conv. | *Selectivity/yield (%) | | | |
| Ex. | Cat. | empirical formula | Alcohol | $N_2$/air/water | (°C.) | (%) | $C_3H_6$ | $C_3H_6O$ | Ac | AA | C3-O |
| E8 | 1 | $Mo_1Sb_1V_{0.3}O_n$ | 1-propanol | 15/5/0 | 375 | 96 | 10 | 64 | 1 | 0 | 65 |
| E9 | 4 | Z1: $W_1Sb_1O_n$ | 1-propanol | Z1: 15/5/0 | Z1: 350 | 100 | 22 | 1 | 1 | 47 | 49 |
| | 1 | Z2: $Mo_1Sb_1V_{0.3}O_n$ | | Z2: 5/2/8 | Z2: 400 | | | | | | |
| E10 | 4 | Z1: $W_1Sb_1O_n$ | 2-propanol | Z1: 15/5/0 | Z1: 325 | 100 | 28 | 1 | 1 | 54 | 56 |
| | 1 | Z2: $Mo_1Sb_1V_{0.3}O_n$ | | Z2: 5/2/8 | Z2: 410 | | | | | | |
| E11 | 4 | $W_1Sb_1O_n$ | 1,2-propanediol | 20/10/8 | 350 | 100 | 3 | 54 | 4 | 1 | 59 |
| E12 | 1 | $Mo_1Sb_1V_{0.3}O_n$ | 1,2-propanediol | 20/10/8 | 450 | 100 | 40 | 17 | 1 | 2 | 20 |
| E13 | 4 | $W_1Sb_1O_n$ | 1,3-propanediol | 20/10/8 | 300 | 100 | 1 | 80 | 2 | 0 | 82 |
| E14 | 1 | $Mo_1Sb_1V_{0.3}O_n$ | 1,3-propanediol | 20/10/8 | 450 | 100 | 8 | 8 | 19 | 6 | 33 |
| C6 | CC5 | $Mo_1V_{0.3}Te_{0.2}Nb_1O_n$ | 1,2-propanediol | 20/10/8 | 375 | 100 | 2 | 0 | 0 | 4 | 4 |
| C7 | CC5 | $Mo_1V_{0.3}Te_{0.2}Nb_1O_n$ | 1,3-propanediol | 20/10/8 | 375 | 100 | 2 | 1 | 2 | 6 | 9 |

*Acetone and C1-2 oxidation products are not reported; $C_3H_6$ = propene, $C_3H_6O$ = propyl aldehyde, Ac = Acrolein, AA = acrylic acid, C3-O = total C3 aldehydes and AA; Z1 = zone-1, Z2 = zone-2; CC5 is Comp. Cat. 5 in Table 2

Example 13 and 14

Solid mixed metal oxides coded as Catalyst-4 and Catalyst-1 in Table 1 were subjected to the evaluation of the catalytic performance in a similar manner as described in Example-1, except 1,3-propanediol was used in the place of isobutanol. The resulting 1,3-propanediol conversion, selectivity values and yields of the valuable C3 products are shown in Table 4.

Comparative Examples 6 and 7

Solid mixed metal oxides coded as Comparative Catalyst-5 in Table 2 were subjected to the evaluation of catalytic performance in a similar manner as described in Example-1, except 1,2-propanediol and 1,3-propanediol, respectively, were used in the place of isobutanol. The resulting propanediol conversion, selectivity values and yields of the valuable C3 products are shown in Table 4.

The entire disclosure of every patent and non-patent publication cited in the foregoing specification is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. The supported, mixed metal oxide catalyst, its methods of preparation and use can in alternate embodiments, be more specifically defined by any of the transitional terms "comprising", "consisting essentially of" and "consisting of".

What is claimed is:

1. A process for producing at least one of an alkene, an aldehyde, and an unsaturated carboxylic acid, comprising subjecting a feed gas mixture of a primary aliphatic alcohol or a diol having a carbon number between 3 to 5 and one or more co-feed gases, which comprises air or oxygen or nitrogen, and, optionally, one or more other suitable diluting gases, to a vapor phase reaction in a heated reactor in the presence of a catalyst system having at least two or more catalytic zones, wherein each of said at least two catalytic zones comprising each of:
   i) a compound of the formula $A_aSb_bX_xY_yZ_zO_n$ wherein A is Mo or W, X is an element selected from the group consisting of Ca, Ce, Co, Fe, Ga, Mg, Ni, Sn, V, W and Zn, Y is one selected from the group consisting of Ag, Au, B, Cr, Cu, La, Li, Mg, Mn, Mo, Na, Nb, Ni, P, Pb, Rb, Re, Ru, Ti, and Z is one from the X or Y groups or from the following: Ba, Cs, K, Pd, Pt and Sr, and wherein $a=1$, $0.05<b<1.5$, $0.01<x<1$, $0\leq y<0.5$, $0\leq z<0.2$ and n is dependent on the oxidation state of the other elements;
   ii) a compound of the formula $A_aX_xY_yZ_zO_n$ wherein A is Mo or W, X is an element selected from the group consisting of Ca, Ce, Co, Fe, Ga, Mg, Ni, Sb, Sn, V, W and Zn, Y is one selected from the group consisting of Ag, Au, B, Cr, Cu, La, Li, Mg, Mn, Mo, Na, Nb, Ni, P, Pb, Rb, Re, Ru, Ti, and Z is one from the X or Y groups or from the following: Ba, Cs, K, Pd, Pt and Sr, and wherein $a=1$, $0.05<x<1.5$, $0\leq y<1$, $0\leq z<0.5$ and n is dependent on the oxidation state of the other elements.

2. The process according to claim 1, wherein said primary aliphatic alcohol or a diol is either 1-propanol or 1,2-propanediol or 1,3-propanediol or a mixture thereof and the resulting alkene is propylene and the resulting aldehyde is propan-1-al and/or 2-propen-1-al (acrolein) and the unsaturated acid is acrylic acid.

3. The process according to claim 1, wherein said primary aliphatic alcohol is 1-propanol and the resulting alkene is propylene and the resulting aldehyde is propan-1-al and/or 2-propen-1-al (acrolein) and the unsaturated acid is acrylic acid.

4. The process according to claim 1, wherein said primary aliphatic alcohol is isobutanol, and the resulting alkene is isobutylene and the resulting aldehyde is 2-methyl-2-propan-1-al and/or 2-methyl-2-propen-1-al (methacrolein) and the unsaturated acid is methacrylic acid.

* * * * *